United States Patent
Cheung

(10) Patent No.: US 7,148,328 B2
(45) Date of Patent: Dec. 12, 2006

(54) COMPOSITIONS AND METHODS FOR REGULATING AUTOLYTIC PROCESSES IN BACTERIA

(75) Inventor: Ambrose Cheung, Hanover, NH (US)

(73) Assignee: Trustees of Dartmouth College, Hanover, NH (US)

( * ) Notice: Subject to any disclaimer, the term of this patent is extended or adjusted under 35 U.S.C. 154(b) by 107 days.

(21) Appl. No.: 10/469,477

(22) PCT Filed: Mar. 6, 2002

(86) PCT No.: PCT/US02/06844

§ 371 (c)(1),
(2), (4) Date: Aug. 27, 2003

(87) PCT Pub. No.: WO02/070666

PCT Pub. Date: Sep. 12, 2002

(65) Prior Publication Data

US 2004/0102624 A1 May 27, 2004

Related U.S. Application Data

(60) Provisional application No. 60/329,140, filed on Oct. 12, 2001, provisional application No. 60/312,546, filed on Aug. 15, 2001, provisional application No. 60/273,791, filed on Mar. 6, 2001.

(51) Int. Cl.
*A61K 38/16* (2006.01)
(52) U.S. Cl. .................... 530/358; 530/350; 536/24.1; 536/24.2
(58) Field of Classification Search ........... 530/350, 530/358; 536/24.1, 24.2
See application file for complete search history.

(56) References Cited

OTHER PUBLICATIONS

Fournier et al. (Journal of Bacteriology, 2000, vol. 182, No. 14, pp. 3955-3964).*
Fujimoto et al. (Journal of Bacteriology, 2000, vol. 182, No. 14, pp. 4822-4828).*
Watson et al "Molecular Biology of the Gene" 4th Edition (1987) Benjamin-Cummings Publishing Company, Inc. USA, p. 608.*
Foster S.J., "Molecular Characterization and Functional Analysis of the Major Autolysin of *Staphylococcus aureus* 8325/4", Journal of Bacteriology 1995 177(19):5723-2725.
Ramadurai et al., "Molecular Cloning, Sequencing, and Expression of *lytM*, a Unique Autolytic Gene of *Staphylococcus aureus*", Journal of Bacteriology 1997 179(11):3625-3631.
Rice et al., "Description of Staphylococcus Serine Protease (ssp) Operon in *Staphylococcus aureus* and Nonpolar Inactivation of sspA-Encoded Serine Protease", Infection and Immunity 2001 69(1):159-169.
Schrader-Fischer et al., "The AbcA Transporter of *Staphylococcus aureus* Afflects Cell Autolysis", Antimicrobial Agents and Chemotherapy 2001 45(2):407-412.
Pan et al., "Cloning and Characterization of the *parC* and *parE* Genes of *Streptococcus pneumoniae* Encoding DNA Topoisomerase IV:Role in Fluroquinolone Resistance", J. Bacteriology 1996 178(14):4060-4069.
NCBI Genome Project—Complete Microbial Genomes [A]-25, [B]-269.

* cited by examiner

*Primary Examiner*—Robert A. Zeman
(74) *Attorney, Agent, or Firm*—Licata & Tyrrell P.C.

(57) ABSTRACT

A nucleic acid sequence required for regulating the autolytic activity of bacteria is provided. Also provided are polypeptides encoded by the gene or mutant gene as well as vector and host cells for expressing these polypeptides. Methods for identifying and using agents which interact with the gene or mutant gene or polypeptides encoded thereby to inhibit bacterial growth and infectivity are also provided.

1 Claim, 1 Drawing Sheet

SEQUENCE LISTING

<160> NUMBER OF SEQ ID NOS: 4

<210> SEQ ID NO 1
<211> LENGTH: 444
<212> TYPE: DNA
<213> ORGANISM: Staphylococcus aureus
<220> FEATURE:
<221> NAME/KEY: CDS
<222> LOCATION: (1)..(444)
<223> OTHER INFORMATION:

<400> SEQUENCE: 1

```
atg tct gat caa cat aat tta aaa gaa cag cta tgc ttt agt ttg tac      48
Met Ser Asp Gln His Asn Leu Lys Glu Gln Leu Cys Phe Ser Leu Tyr
1               5                   10                  15 aat gct caa aga caa gtt aat cgc tac tac tct aac aaa gtt ttt aag      96
Asn Ala Gln Arg Gln Val Asn Arg Tyr Tyr Ser Asn Lys Val Phe Lys
            20                  25                  30 aag tac aat cta aca tac cca caa ttt ctt gtc tta aca att tta tgg    144
Lys Tyr Asn Leu Thr Tyr Pro Gln Phe Leu Val Leu Thr Ile Leu Trp
        35                  40                  45 gat gaa tct cct gta aac gtc aag aaa gtc gta act gaa tta gca ctc    192
Asp Glu Ser Pro Val Asn Val Lys Lys Val Val Thr Glu Leu Ala Leu
    50                  55                  60 gat act ggt aca gta tca cca tta tta aaa cga atg gaa caa gta gac    240
Asp Thr Gly Thr Val Ser Pro Leu Leu Lys Arg Met Glu Gln Val Asp
65                  70                  75                  80 tta att aag cgt gaa cgt tcc gaa gtc gat caa cgt gaa gta ttt att    288
Leu Ile Lys Arg Glu Arg Ser Glu Val Asp Gln Arg Glu Val Phe Ile
                85                  90                  95 cac ttg act gac aaa agt gaa act att aga cca gaa tta agt aat gca    336
His Leu Thr Asp Lys Ser Glu Thr Ile Arg Pro Glu Leu Ser Asn Ala
            100                 105                 110 tct gac aaa gtc gct tca gct tct tct tta tcg caa gat gaa gtt aaa    384
Ser Asp Lys Val Ala Ser Ala Ser Ser Leu Ser Gln Asp Glu Val Lys
        115                 120                 125 gaa ctt aat cgc tta tta ggt aaa gtc att cat gca ttt gat gaa aca    432
Glu Leu Asn Arg Leu Leu Gly Lys Val Ile His Ala Phe Asp Glu Thr
    130                 135                 140 aag gaa aaa taa                                                    444
Lys Glu Lys
145
```

<210> SEQ ID NO 2
<211> LENGTH: 147
<212> TYPE: PRT
<213> ORGANISM: Staphylococcus aureus

<400> SEQUENCE: 2

```
Met Ser Asp Gln His Asn Leu Lys Glu Gln Leu Cys Phe Ser Leu Tyr
1               5                   10                  15

Asn Ala Gln Arg Gln Val Asn Arg Tyr Tyr Ser Asn Lys Val Phe Lys
            20                  25                  30

Lys Tyr Asn Leu Thr Tyr Pro Gln Phe Leu Val Leu Thr Ile Leu Trp
        35                  40                  45

Asp Glu Ser Pro Val Asn Val Lys Lys Val Val Thr Glu Leu Ala Leu
    50                  55                  60

Asp Thr Gly Thr Val Ser Pro Leu Leu Lys Arg Met Glu Gln Val Asp
65                  70                  75                  80

Leu Ile Lys Arg Glu Arg Ser Glu Val Asp Gln Arg Glu Val Phe Ile
                85                  90                  95

His Leu Thr Asp Lys Ser Glu Thr Ile Arg Pro Glu Leu Ser Asn Ala
            100                 105                 110

Ser Asp Lys Val Ala Ser Ala Ser Leu Ser Gln Asp Glu Val Lys
        115                 120                 125

Glu Leu Asn Arg Leu Leu Gly Lys Val Ile His Ala Phe Asp Glu Thr
    130                 135                 140

Lys Glu Lys
145
```

<210> SEQ ID NO 3
<211> LENGTH: 402
<212> TYPE: DNA
<213> ORGANISM: Staphylococcus aureus
<220> FEATURE:
<221> NAME/KEY: CDS
<222> LOCATION: (1)..(402)
<223> OTHER INFORMATION:

<400> SEQUENCE: 3

```
atg tct gat caa cat aat tta aaa gaa cag cta tgc ttt agt ttg tac      48
Met Ser Asp Gln His Asn Leu Lys Glu Gln Leu Cys Phe Ser Leu Tyr
1               5                   10                  15 aat gct caa aga caa gtt aat cgc tac tac tct aac aaa gtt ttt aag      96
Asn Ala Gln Arg Gln Val Asn Arg Tyr Tyr Ser Asn Lys Val Phe Lys
            20                  25                  30 aag tac aat cta aca tac cca caa ttt ctt gtc tta aca att tta tgg     144
Lys Tyr Asn Leu Thr Tyr Pro Gln Phe Leu Val Leu Thr Ile Leu Trp
        35                  40                  45 gat gaa tct cct gta aac gtc aag aaa gtc gta act gaa tta gca ctc     192
Asp Glu Ser Pro Val Asn Val Lys Lys Val Val Thr Glu Leu Ala Leu
    50                  55                  60 gat act ggt aca gta tca cca tta tta aaa cga atg gaa caa gta gac     240
Asp Thr Gly Thr Val Ser Pro Leu Leu Lys Arg Met Glu Gln Val Asp
65                  70                  75                  80 tta att aag cgt gaa cgt tcc gaa gtc gat caa cgt gaa gta ttt att     288
Leu Ile Lys Arg Glu Arg Ser Glu Val Asp Gln Arg Glu Val Phe Ile
                85                  90                  95 cac ttg act gac aaa agt gaa act att aga cca gaa tta agt aat gca     336
His Leu Thr Asp Lys Ser Glu Thr Ile Arg Pro Glu Leu Ser Asn Ala
            100                 105                 110
```

```
                                                                              -continued
tct gac aaa gtc gct tca gct tct tct tta tcg caa gat gaa gtt aaa              384
Ser Asp Lys Val Ala Ser Ala Ser Ser Leu Ser Gln Asp Glu Val Lys
        115                 120                 125 gaa ctt aat cgc tta tta                                                       402
Glu Leu Asn Arg Leu Leu
    130
```

<210> SEQ ID NO 4
<211> LENGTH: 134
<212> TYPE: PRT
<213> ORGANISM: Staphylococcus aureus

<400> SEQUENCE: 4

```
Met Ser Asp Gln His Asn Leu Lys Glu Gln Leu Cys Phe Ser Leu Tyr
1               5                   10                  15

Asn Ala Gln Arg Gln Val Asn Arg Tyr Tyr Ser Asn Lys Val Phe Lys
                20                  25                  30

Lys Tyr Asn Leu Thr Tyr Pro Gln Phe Leu Val Leu Thr Ile Leu Trp
            35                  40                  45

Asp Glu Ser Pro Val Asn Val Lys Lys Val Val Thr Glu Leu Ala Leu
        50                  55                  60

Asp Thr Gly Thr Val Ser Pro Leu Leu Lys Arg Met Glu Gln Val Asp
65                  70                  75                  80

Leu Ile Lys Arg Glu Arg Ser Glu Val Asp Gln Arg Glu Val Phe Ile
                85                  90                  95

His Leu Thr Asp Lys Ser Glu Thr Ile Arg Pro Glu Leu Ser Asn Ala
                100                 105                 110

Ser Asp Lys Val Ala Ser Ala Ser Ser Leu Ser Gln Asp Glu Val Lys
            115                 120                 125

Glu Leu Asn Arg Leu Leu
        130
```

US 7,148,328 B2

COMPOSITIONS AND METHODS FOR REGULATING AUTOLYTIC PROCESSES IN BACTERIA

INTRODUCTION

This application claims the benefit of priority from U.S. provisional application Serial No. 60/273,791, filed on Mar. 6, 2001; Ser. No. 60/312,546, filed on Aug. 15, 2001; and Ser. No. 60/329,140, filed on Oct. 12, 2001, whose contents are incorporated herein by reference in their entireties.

This invention was made in the course of research sponsored by the National Institute of Health (NIH Grant No. RO1-AI37142). The U.S. government may have certain rights in this invention.

BACKGROUND

*Staphylococci* are hardy and ubiquitous colonizers of human skin and mucous membranes and were among the first human pathogens identified. These bacteria constitute a medically important genera of microbes as they are known to produce two types of disease, invasive and toxigenic.

Invasive infections are characterized generally by abscess formation affecting both skin surfaces and deep tissues. In addition, *Staphylococcus aureus* (*S. aureus*) is the second leading cause of bacteremia in cancer patients. Osteomyelitis, septic arthritis, septic thrombophlebitis and acute bacterial endocarditis are also relatively common.

There are also at least three clinical conditions resulting from the toxigenic properties of *Staphylococci*. The manifestation of these diseases result from the actions of exotoxins as opposed to tissue invasion and bacteremia. These conditions include: Staphylococcal food poisoning, scalded skin syndrome and toxic shock syndrome.

*S. aureus* are non-mobile, non-sporulating gram-positive cocci 0.5–1.5 im in diameter, that occur singly and in pairs, short chains, and irregular three-dimensional clusters. *S. aureus* can grow over a wide range of environmental conditions, but they grow best at temperatures between 30° C. and 37° C. and at a neutral pH. They are resistant to desiccation and to chemical disinfection, and they tolerate NaCl concentrations up to 12%. It has been found that the growth of the *S. aureus* becomes unusually sensitive to a high-NaCl concentration by decreasing the $Ca^{2+}$ concentration in growth media allowing for autolysis (Ishikawa, *Microbiology and Immunology*, 2000: 44(2):97–104).

Humans constitute the major reservoir of the *S. aureus* bacteria. The cross sectional carriage rate in adults is 15 to 40 percent. The mucous membranes of the anterior nasopharynx are the principal site of carriage. Other sites include the axillae, the vagina, the perineum and occasionally the gastrointestinal tract. Colonization by *S. aureus* may be intermittent or persistent and is probably influenced by both microbial and host factors as well as by the nature of the competing non-*Staphylococcal* flora.

The frequency of *S. aureus* infections has risen dramatically in the past 20 years. This has been attributed to the emergence of multiple antibiotic resistant strains and an increasing population of people with weakened immune systems. It is no longer uncommon to isolate *S. aureus* strains which are resistant to some or all of the standard antibiotics. This has created a demand for both new antimicrobial agents and diagnostic tests for this organism. Accordingly, there is a need for better understanding of factors which regulate infectivity and growth of *S. aureus*.

Genes identified as involved in the infectivity and/or growth of *S. aureus* include the ArlS regulator, involved in adhesion (Fournier and Hooper, *Journal of Bacteriology*, 2000: 182(14):3955–64), the pbpC gene, which affects the rate of autolysis, (Pinho et al., *Journal of Bacteriology*, 2000: 182(4):1074–9), lytRS (Brunskill and Bayles, *Journal of Bacteriology*, 1996: 178(19):5810–2), lrgA and lrgB (Fujimoto et al., *Journal of Bacteriology*, 2000: 182(17): 4822–8), and lytM identified in autolysis-deficient mutants of *S. aureus* (Ramadurai and Jayaswal, *Journal of Bacteriology*, 1997: 179(11):3625–31).

A new genetic locus of *S. aureus* which regulates autolytic processes has now been identified. The gene at this locus, referred to herein as RAT, regulator of autolytic activity, which regulates autolytic processes, has been cloned and sequenced. The phrase, "which regulates expression of polypeptides involved in autolytic processes" used herein means that the gene or polypeptide encoded by the gene controls, modulates or regulates the expression of polypeptides involved in autolytic processes such as autolytic enzymes (e.g., murein hydrolase, cell wall hydrolase, glycylglycine endopeptidase), polypeptides involved in environmental signaling, the secretion of autolysins, or other autolytic processes. Further, it has been shown that a mutation at this site renders *S. aureus* more susceptible to lysis with antibiotics.

SUMMARY OF THE INVENTION

The present invention provides a new genetic locus of *S. aureus* and other bacteria that is involved in the control, modulation or regulation (these latter three terms are used as equivalents herein) of autolytic activity and processes in bacteria. Examples of the gene, a mutant of the gene, as well as the polypeptides encoded by the gene and the mutant of the gene are also provided.

An object of the present invention is to provide nucleic acid sequences isolated from *S. aureus* and other bacteria which regulate autolytic activity in bacteria. The nucleic acid sequences referred to herein are the RAT gene (SEQ ID NO:1), the RAT mutant gene (SEQ ID NO:3) or fragments thereof. In a preferred embodiment, the nucleic acid sequence is the RAT gene (SEQ ID NO:1).

Another object of the present invention is to provide polypeptides encoded by the RAT gene and vectors and host cells comprising nucleic acid sequences encoding these polypeptides. In a preferred embodiment, the polypeptide has the sequence of SEQ ID NO:2. The sequence of the polypeptide encoded by the mutant of the RAT gene is also provided (SEQ ID NO:4).

Another object of the present invention is to provide a vector which comprises a transposon element and a polynucleotide sequence which encodes the RAT polypeptide (SEQ ID NO:2) or the RAT mutant polypeptide (SEQ ID NO:4) and host cells comprising this vector.

Another object of the present invention is to provide a method of identifying agents that modulate autolytic activity of *S. aureus* and other bacteria through interaction with the RAT gene (SEQ ID NO:1) or RAT mutant gene (SEQ ID NO:3) or polypeptides encoded by RAT or the RAT mutant gene. These agents are expected to be useful in the inhibition of growth of *S. aureus* and other bacteria and in the treatment of hosts infected by *S. aureus* and other bacteria. These agents can be used alone or in combination with an antibiotic such as penicillin to promote lysis of the bacteria.

Accordingly, another object of the present invention is to provide methods for modulating autolytic activity of *S.* aureus and other bacteria to inhibit their growth and infectivity by contacting the bacteria with an agent which interacts with the RAT gene (SEQ ID NO:1) or RAT mutant gene (SEQ ID NO:3) or polypeptides encoded thereby.

Yet another object of the present invention is to provide anti-bacterial agents which comprise a compound which prevents or inhibits infections by *S. aureus* or other bacteria via interaction with the RAT gene (SEQ ID NO:1) or RAT mutant gene (SEQ ID NO:3) or polypeptides encoded by RAT or the RAT mutant gene.

Another object of the present invention is to provide a kit for identifying the presence of the RAT gene (SEQ ID NO:1) or RAT mutant gene (SEQ ID NO:3) or the polypeptides they encode (SEQ ID NO:2 or SEQ ID NO:4, respectively).

DETAILED DESCRIPTION OF THE INVENTION

*S. aureus* is the most prevalent human pathogen in the *Staphylococcal* genus. It remains a major public health concern due to its tenacity, potential destructiveness and increasing resistance to antimicrobial agents. Much research has been focused on identifying genes or gene products of *S. aureus* which serve as targets in the development of new antibacterial agents.

Using transposon mutagenesis, a gene referred to herein as RAT (regulator of autolytic activity)(SEQ ID NO:1), which is specifically involved in regulation of autolytic activity of *S. aureus*, has been identified. To identify the RAT gene, a Tn551 transposon library of *S. aureus* strain RN6390 was constructed. The library was screened for genes that affected expression of genes encoding the capsular polysaccharide (cap genes—16 genes encoded within the cap operon) of *S. aureus*. Using the cap promoter linked to the GFP reporter gene (green fluorescent protein), a mutant was identified that displayed significantly lower cap promoter activity. However, upon growing this mutant, it was discovered that this strain grew poorly in 03GL medium, reaching a maximum optical density of 0.8 when the parental strain could achieve an OD650 nm of 1.3. The defect was linked to the transposon insertion because this phenotype could be back-crossed into the parental strain. The region of the mutant chromosome where the transposon was inserted was subsequently sequenced; the sequence of the mutant locus is SEQ ID NO:3. This gene was designated RAT, or regulator of autolytic activity. The RAT mutant gene encodes a protein of 134 residues in length. The RAT mutant is a transposon mutant in which a Tn551 transposon is inserted at the 3' end of the polynucleotide sequence, yielding a truncated protein or polypeptide missing the last 13 amino acid residues of the wild-type protein. It is believed that the RAT mutant is a partial gene knockout which enables the bacteria to survive. By "knock-out" it is meant that an alteration in the target gene sequence occurs which results in a decrease of function of the target gene.

Zymogram analysis revealed that the RAT mutant strain displayed significantly enhanced autolytic activity as compared with the parent. This defect in autolytic activity was restored upon complementation of the mutant with a single copy of the RAT gene inserted into the mutant chromosome. RAT was cloned and sequenced (SEQ ID NO:1). RAT encodes a 17 kDa protein of 147 residues in length. Forty-seven of the 147 residues (32%) are charged and the pI of RAT is predicted to be 7.38.

Figure 1:
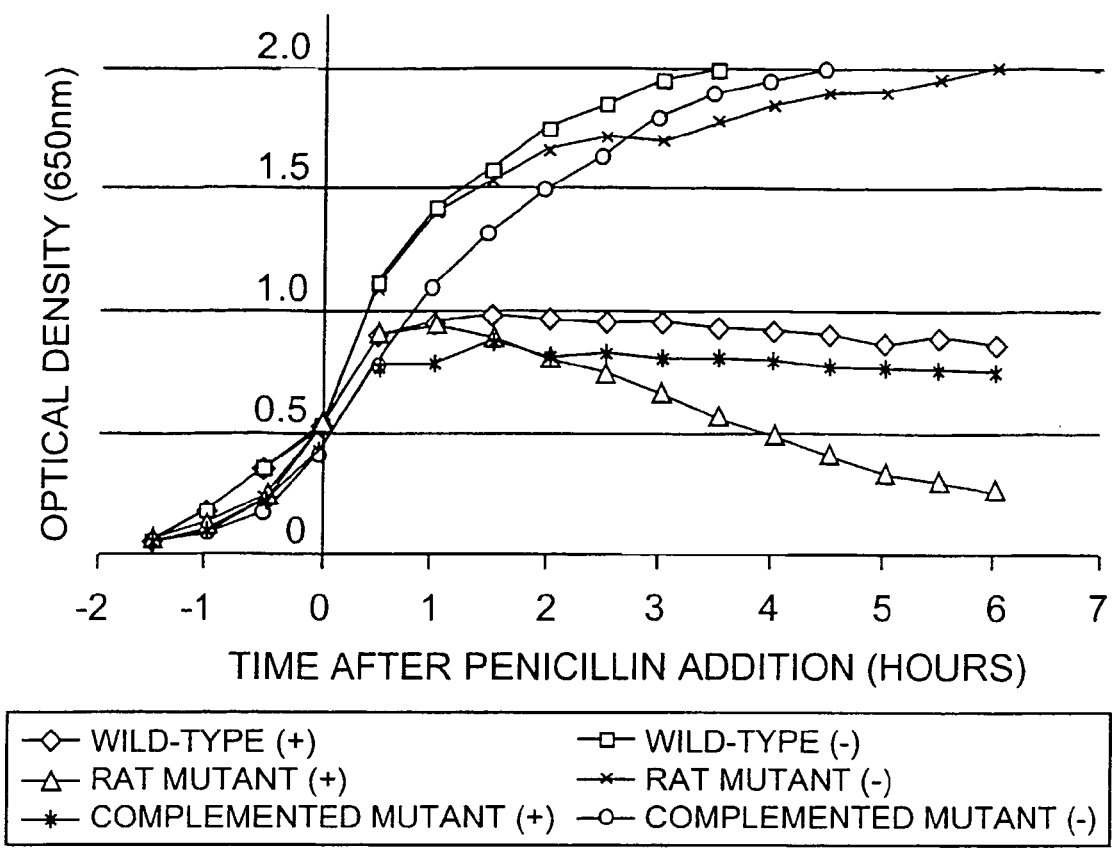
FIG. 1 graphically demonstrates the effect that subinhibitory concentrations of penicillin have on the RAT mutant as compared to wild-type.

RAT plays a role in regulating autolytic activity of *S. aureus*. More specifically, in the presence of penicillin, the RAT mutant was shown to readily increase lysis as compared to wild-type *S. aureus*. Furthermore, inactivation of the RAT locus was shown to render the *S. aureus* bacteria sensitive to lysis upon growth beyond the mid-log phase. To evaluate whether the cell lysis of the RAT mutant was additive to the effect of a subinhibitory concentration of penicillin, 200 ng/ml of penicillin was added to a growing culture of the RAT mutant at an OD650 nm of 0.5, corresponding to the mid-log phase. Contrary to the wild-type strain that displayed no increase in optical density (i.e., no growth) upon addition of penicillin, the RAT mutant exhibited a further reduction in optical density as the growth cycle progressed (FIG. 1). This finding is consistent with the additive effect of penicillin upon the lytic propensity of the RAT mutant late in the growth cycle. Similar results were obtained using gentamicin and cephalothin. In plating these cultures on agar plates without antibiotic selection, it was found that the RAT mutant has 1–2 log more kill than the parental strain. In comparison to the parental strain without antibiotics, the RAT mutant with subinhibitory concentrations of penicillin has a 3–4 log kill.

To analyze the autolytic activity of the RAT mutant, zymographic analysis of cell-associated murein hydrolases was performed. Bacterial cells were centrifuged, washed, and resuspended in SDS-gel loading buffer, heated for 3 minutes at 100° C., recentrifuged, and the supernatant applied to a SDS-gel containing heat-killed *S. aureus* RN4220. Following electrophoresis, the gel was soaked in 0.1 percent Triton X100 at 37° C. overnight to hydrolyze RN4220 cells that had been attacked by autolytic enzymes in the cell extracts. After incubation, the gel was stained with one percent methylene blue and destained in water. Clear bands, indicating zones of murein hydrolase activity were found to be enhanced in the RAT mutant as compared with the wild-type control. As a positive control, a sarA mutant was utilized. The sarA gene normally represses murein hydrolase activity.

Figure 2:
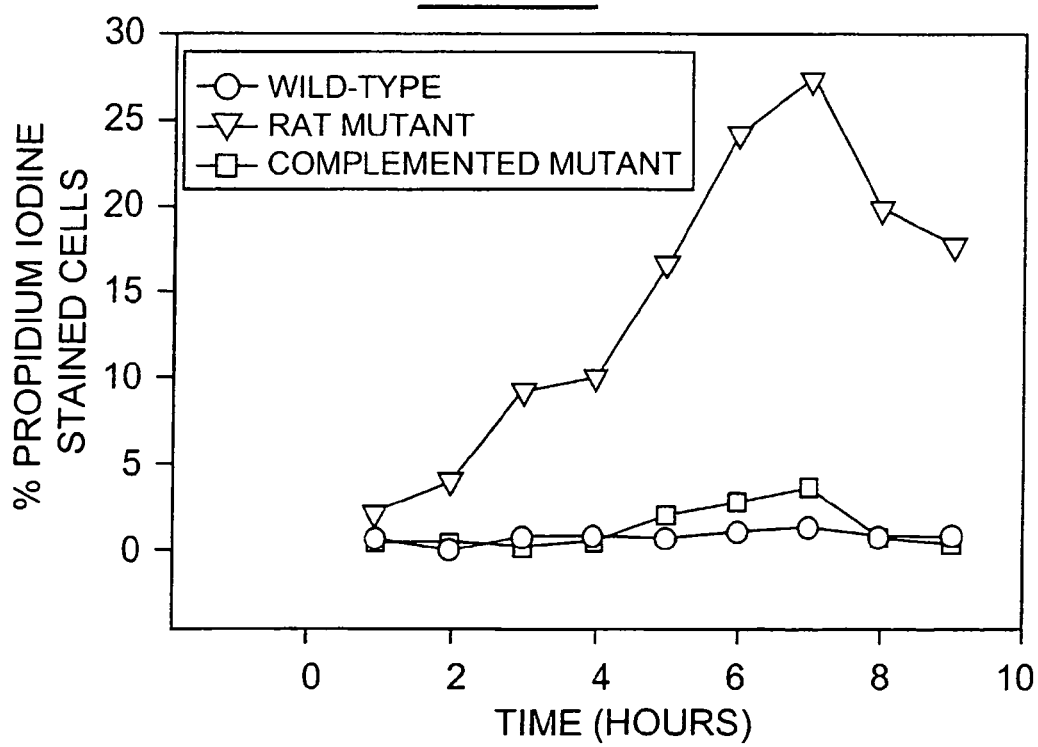
FIG. 2 graphically represents the viability of the RAT mutant as compared to wild-type by propidium iodide staining.

To assess the viability of RAT mutant cells late in the growth cycle, the bacterial cells obtained from different parts of the growth cycle were stained with propidium iodide. Penetration of the cell with propidium iodide indicates cell death or necrosis. Many of the RAT mutant cells picked up the propidium iodide stain as the growth cycle lengthened (FIG. 2), thus accounting for the decrease in optical densities in the RAT mutant during the late log phase.

The cell wall morphology of the RAT mutant strain differs from the wild-type strain. RAT mutant cells, undergoing division, exhibited a thicker cell wall than the wild-type strain. The outer contour of the RAT mutant was rough while the surface of the wild type cells was smooth. Irregularities in the outer cell wall have previously been associated with altered autolytic activities in mutants. Bacterium possessing nucleotide sequences with a sufficient degree of homology to SEQ ID NO:3 also will exhibit an increase sensitivity to lysis.

The bacterial cell wall is maintained by competing enzymes involved in the synthesis and lysis of the cell wall. Examples of autolytic enzymes include glucosamidase, muramidase, amidase, and endopeptidase. The synthesis of bacterial cell walls is a dynamic process requiring the precise regulation of both synthetic and autolytic activities. The autolytic activity of many bacteria is carefully controlled during the growth cycle in particular by regulatory elements. A disruption of these regulatory elements alters autolytic activity and leads to premature cell lysis during growth. The RAT mutant has a defect in autolytic activity which prevents the mutant from reaching the stationary phase of growth. By northern blot analysis, it was shown that the RAT mutation had an effect on the expression of autolytic enyzmes such as lytN, lytM, and atl. The novel cell wall hydrolase, lytN, and the glycylglycine endopeptidase, lytM, are up-regulated by the RAT mutation. Conversely, the RAT mutation down-regulated the regulators of autolytic activity, namely, lytS, lytR, lrgA, lrgB, arlR, and arlS. Furthermore, the RAT mutation affects the expression of certain other *S. aureus* genes, e.g., hla, spa, abcA, scdA, pbp2, pbp4, and sspA. Both hla and scdA expression are down-regulated by the RAT mutation, whereas both spa and abcA expression are up-regulated by the RAT mutation.

In a comparison of the RAT gene sequence with the genomes of other microbes, homologs with significant sequence similarity were identified. The RAT gene or a homolog thereof performs a role in regulating the autolytic activity of bacteria, including but not limited to: *Staphylococcus aureus* (such as *Staphylococcus aureus* N315, *Staphylococcus aureus* strain Mu50, *Staphylococcus aureus* strain NCTC 8325, *Staphylococcus aureus* MSSA strain, *Staphylococcus aureus* MRSA strain, *Staphylococcus aureus* COL, *Staphylococcus epidermidis*, and *Staphylococcus sciuri*), *Sinorhizobium* species (e.g., *meliloti*), *Listeria* species (e.g., *monocytogenes*),*Clostridium* species (e.g., *acetabutylicum, difficile*), *Vibrio* species (e.g., *cholerae*), *Corynebacterium* species (e.g., *diptheriae*), *Brucella* species (e.g., *suis*), *Pseudomonas* species (e.g., *aeruginosa, syringae, putida*), *Shewanella* species (e.g., *putrefasciens*), *Mesorhizobium* species (e.g., *loti*), *Caulobacter* species (e.g., *crescentus*), *Lactococcus* species (e.g., *lactis*), *Mycobacterium* species (e.g., *smegmatis, leprae, tuberculosis*), *Burkholderia* species (e.g., *mallei, pseudomallei*), *Geobacter* species (e.g., *sulfurreducens*), *Treponema* species (e.g., *denticola*), *Bacillus* species (e.g., *stearothermophilus, anthracis, subtilis, halodurnas*), *Escherichia* species (e.g., *coli*), *Enterococcus* species (e.g., *faecalis*), *Salmonella* species (e.g., *dublin, enteriditis, paratyphi, typhi*), *Klebsiella* species (e.g., *pneumoniae*), *Bordetella* species (e.g., *parapertussis*), *Actinobacillus*species (e.g., *actinomycetemcomitans*), *Streptomyces* species (e.g., *coelicolor*), *Streptococcus* species (e.g., *pyogenes, pneumoniae*) and *Acinetobacter* species.

Useful homologous sequences are those which encode a polypeptide which increases bacterial susceptibility to autolysis or increased lysis due to antibiotic administration. In a preferred embodiment the polynucleotide sequence is at least 40 percent homologous to the SEQ ID NO:1 or SEQ ID NO:3. In a more preferred embodiment the polynucleotide sequence is at least 60 percent homologous to the SEQ ID NO:1 or SEQ ID NO:3. In a most preferred embodiment the polynucleotide sequence is at least 80 percent homologous to the SEQ ID NO:1 or SEQ ID NO:3.

The present invention includes the nucleic acid sequences for the RAT gene and RAT mutant gene and polypeptides encoded thereby. For purposes of the present invention, polypeptides encoded by the RAT gene and RAT mutant gene are referred to herein as RAT polypeptides and RAT mutant polypeptides, respectively. Exemplary nucleic acid sequences of the present invention are SEQ ID NO:1 and SEQ ID NO:3. However, by the term "nucleic acid sequence" it is meant to include any form of DNA or RNA such as cDNA or genomic DNA or mRNA, respectively, encoding a RAT polypeptide or RAT mutant polypeptide, or an active fragment thereof which are obtained by cloning or produced synthetically by well-known chemical techniques. DNA may be double- or single-stranded. Single-stranded DNA may comprise the coding or sense strand or the non-coding or antisense strand. Thus, the term nucleic acid sequence also includes sequences which hybridize under stringent conditions to the above-described polynucleotides. As used herein, the term "stringent conditions" means at least 60% homology at hybridization conditions of 60° C. at 2×SSC buffer.

In a preferred embodiment, the nucleic acid sequence comprises the cDNA of SEQ ID NO:1 or a homologous sequence or fragment thereof which encodes a polypeptide having similar activity to the polypeptide (SEQ ID NO:2) encoded by RAT. In another preferred embodiment, the nucleic acid sequence comprises the cDNA of SEQ ID NO:3 or a homologous sequence or fragment thereof which encodes a polypeptide having similar activity to the polypeptide (SEQ ID NO:4) encoded by the RAT mutant gene. Due to the degeneracy of the genetic code, nucleic acid sequences of the present invention may also comprise other nucleic acid sequences encoding the RAT polypeptide or RAT mutant polypeptide and derivatives, variants or active fragments thereof. The present invention also relates to variants of these nucleic acid sequences which may be naturally occurring, i.e., allelic variants, or mutants prepared by well known mutagenesis techniques.

The present invention also relates to a conditional mutant whereby the RAT gene or RAT mutant gene can be expressed under an inducible promoter.

The present invention also relates to vectors comprising nucleic acid sequences of the present invention and host cells which are genetically engineered with these vectors to produce active RAT polypeptides or RAT mutant polypeptides, or fragments thereof. Generally, any vector suitable to maintain, propagate or express the nucleic acid sequences of this invention in a host cell may be used for expression in this regard.

The nucleic acid sequences and polypeptides of the present invention, as well as vectors and host cells expressing the polypeptides are useful as research tools to enhance the understanding of the autolytic process of *S. aureus* and other bacteria. The methods and compositions of the present invention are believed to be effective in other bacteria having significant homology with the polynucleotide sequence of RAT or the RAT mutant.

Further, these compositions are useful in the identification of agents which interact with either the RAT gene or RAT mutant gene, or polypeptides encoded thereby to modulate autolytic activity of the bacteria. By "interact" it is meant that the agent increases or decreases expression of the RAT gene or RAT mutant gene, or increases or decreases activity of a RAT polypeptide or RAT mutant polypeptide. In a preferred embodiment, agents will decrease, interfere with or inhibit RAT gene or RAT mutant gene expression or decrease, interfere with or inhibit the activity of a RAT polypeptide or RAT mutant polypeptide so that the bacteria is lysed more easily. Examples of such agents include, but are not limited to, antisense molecules or ribozymes targeted to the RAT gene or RAT mutant gene which inhibit the gene expression, means for introduction of mutations into the RAT gene or RAT mutant gene which inhibit gene expression or produce a polypeptide with decreased activity, and small organic molecules or peptides which are capable of inhibiting activity of the RAT polypeptides or RAT mutant polypeptides or the genes themselves (e.g., by binding to the promoter region of the gene to inhibit transcription and subsequent expression). The active site of the RAT polypeptide, could be used to simulate activity in the mutant. Alternatively, a small compound library can be used to screen for agents which augment the lytic activity of the RAT gene or RAT mutant gene. This augmentation of lytic activity can be monitored by binding of the small compound to the RAT polypeptide or RAT mutant polypeptide and determining the ability of the small compound to induce cell lysis.

Accordingly, one aspect of the present invention provides an analog library to produce a very large number of potential molecules for regulating the RAT expression system, and in general the greater the number of analogs in the library, the greater the likelihood that at least one member of the library will effectively regulate the RAT expression system. Designed libraries following a particular template structure and limiting amino acid variation at particular positions are much preferred, since a single library can encompass all the designed analogs and the included sequences will be known and presented in roughly equal numbers. By contrast, random substitution at only six positions in an amino acid sequence provides over 60 million analogs, which is a library size that begins to present practical limitations even when utilizing screening techniques as powerful as phage display. Libraries larger than this would pose problems in handling, e.g., fermentation vessels would need to be of extraordinary size, and more importantly, the likelihood of having all of the planned polypeptide sequence variations represented in the prepared library would decrease sharply. It is therefore preferred to create a designed or biased library, in which the amino acid positions designated for variation are considered so as to maximize the effect of substitution on the RAT or RAT mutant regulation characteristics of the analog, and the amino acid residues allowed or planned for use in substitutions are limited.

The use of replicable genetic packages, such as the bacteriophages, is one method of generating novel polypeptide entities that regulate RAT or RAT mutant expression. This method generally consists of introducing a novel, exogenous DNA segments into the genome of a bacteriophage (or other amplifiable genetic package) so that the polypeptide encoded by the non-native DNA appears on the surface of the phage. When the inserted DNA contains sequence diversity, then each recipient phage displays one variant of the template (parental) amino acid sequence encoded by the DNA, and the phage population (library) displays a vast number of different but related amino acid sequences.

Such techniques make it possible not only to screen a large number of potential binding molecules but make it practical to repeat the binding/elution cycles and to build secondary, biased libraries for screening analog-displaying packages that meet initial criteria.

It is well-known to those normally skilled in the art that it is possible to replace peptides with peptidomimetics. Peptidomimetics are generally preferable as therapeutic agents to peptides owing to their enhanced bioavailability and relative lack of attack from proteolytic enzymes. Accordingly, the present invention also provides peptidomimetics and other lead compounds which can be identified based on data obtained from structural analysis of the RAT or the RAT mutant. A potential analog may be examined through the use of computer modeling using a docking program such as GRAM, DOCK, or AUTODOCK. This procedure can include computer fitting of potential analogs. Computer programs can also be employed to estimate the attraction, repulsion, and steric hindrance of an analog to a potential binding site. Generally the tighter the fit (e.g., the lower the steric hindrance, and/or the greater the attractive force) the more potent the potential drug will be since these properties are consistent with a tighter binding constant. Furthermore, the more specificity in the design of a potential drug the more likely that the drug will not interfere with other properties of the RAT expression system. This will minimize potential side-effects due to unwanted interactions with other proteins.

Initially a potential analog could be obtained by screening a random peptide library produced by a recombinant bacteriophage, for example, or a chemical library. An analog ligand selected in this manner could be then be systematically modified by computer modeling programs until one or more promising potential ligands are identified.

Such computer modeling allows the selection of a finite number of rational chemical modifications, as opposed to the countless number of essentially random chemical modifications that could be made, and of which any one might lead to a useful drug. Thus, the three-dimensional structure and computer modeling, a large number of compounds may be rapidly screened and a few likely candidates may be determined without the laborious synthesis of untold numbers of compounds.

Once a potential peptidomimetic or lead compound is identified it can be either selected from a library of chemicals commercially available from most large chemical companies including Merck, GlaxoWelcome, Bristol Meyers Squib, Monsanto/Searle, Eli Lilly, Novartis and Pharmacia UpJohn, or alternatively the potential ligand is synthesized de novo. As mentioned above, the de novo synthesis of one or even a relatively small group of specific compounds is reasonable in the art of drug design.

Agents of the present invention may comprise antibodies against the RAT polypeptide or RAT mutant polypeptide. Antibodies against the RAT polypeptide or RAT mutant polypeptide can facilitate selective delivery of a cytotoxic agent to *S. aureus* or other bacteria. Alternatively, antibodies can serve as the agent, binding to the RAT polypeptide or RAT mutant polypeptide thereby inhibiting activity. The RAT polypeptides or RAT mutant polypeptide, or epitope bearing fragments thereof can be used as immunogens to produce antibodies immunospecific for such polypeptides. Various techniques well known in the art can be used routinely to produce antibodies (Kohler, G. and Milstein, C., *Nature* 1975: 256: 495–497; Kozbor et al., *Immunology Today*, 1983: 4: 72; Cole et al., *Monoclonal Antibodies and Cancer Therapy*, 1985: pp 77–96).

Accordingly, the present invention also relates to agents identified as inhibitors of RAT gene or RAT mutant gene expression or RAT polypeptide or RAT mutant polypeptide activity and methods for using these agents to increase lysis of *S. aureus* and other bacteria, thereby inhibiting their growth and infectivity. These agents can be incorporated into a pharmaceutical composition and administered to a host to inhibit growth and infectivity of *S. aureus* and other bacteria in the host. The term "host" as used herein includes humans.

Pharmaceutical compositions of the present invention comprise an effective amount of an agent which inhibits the expression of the RAT gene or RAT mutant gene or an activity of the RAT polypeptide or RAT mutant polypeptide and a pharmaceutically acceptable vehicle. By "effective amount" it is meant an amount which inactivates the RAT gene or RAT mutant gene locus and renders *S. aureus* or other bacteria susceptible to killing through cell lysis. The pharmaceutical compositions can be administered to a host, preferably a human, to inhibit the growth of *S. aureus* or other bacteria in the host. The pharmaceutical composition can be administered alone, or in combination with an antibiotic such as penicillin, gentamicin and cephalothin to enhance killing or lysis of the bacteria. Pharmaceutical compositions of the present invention can be administered by various routes, including, but not limited to, topically, intramuscularly, intraperitoneally, intranasally, orally, subcutaneously, or intravenously.

The present invention also provides a pharmaceutical pack or kit comprising one or more containers filled with one or more of the ingredients of the agents or pharmaceutical compositions of the invention. The kit may be used for identifying the presence of RAT or a RAT mutant gene or RAT polypeptide or RAT mutant polypeptide in a biological sample by analyzing the sample for the presence of RAT or a RAT mutant. Detection of RAT or RAT mutant cells in a sample are indicative of the patient being susceptible to treatment for the bacterial infection using conventional antibiotic treatment, such as penicillin. Associated with such container(s) can be a notice in the form of prescribed by a governmental agency regulating the manufacture, use or sale of pharmaceuticals or biological products, which notice reflects approval by the agency or manufacture, use or sale for human administration. In addition, the polypeptides of the present invention may be employed in conjunction with other therapeutic compounds.

The embodiments herein described are not meant to be limiting to the invention. Those of skill in the art will appreciate the invention may be practiced by using numerous chemical entities and by numerous methods all within the breadth of the following claims.

What is claimed is:

1. An isolated RAT polypeptide comprising the amino acid sequence of SEQ ID NO:2.

* * * * *